United States Patent [19]

Fujiwara et al.

[11] 4,375,511

[45] Mar. 1, 1983

[54] PROCESS TO PRODUCE ACLACINOMYCINS A AND B

[75] Inventors: Akiko Fujiwara; Tatsuo Hoshino, both of Kamakura; Masaaki Tazoe, Yokohama, all of Japan

[73] Assignee: Hoffmann-La Roche Inc., Nutley, N.J.

[21] Appl. No.: 313,534

[22] Filed: Oct. 22, 1981

[30] Foreign Application Priority Data

Oct. 27, 1980 [GB] United Kingdom ............... 8034537

[51] Int. Cl.³ ..................... C12N 1/00; C12P 19/56; C12R 1/465
[52] U.S. Cl. ..................................... 435/78; 435/253; 435/886; 435/169
[58] Field of Search ................. 435/78, 169, 253, 886

[56] References Cited

U.S. PATENT DOCUMENTS

| 4,071,411 | 1/1978 | Umezawa et al. | 435/886 |
| 4,204,038 | 5/1980 | Umezawa et al. | 435/886 |
| 4,209,588 | 6/1980 | Umezawa et al. | 435/886 |
| 4,329,339 | 5/1982 | Fujiwara et al. | 435/78 |

*Primary Examiner*—Esther M. Kepplinger
*Attorney, Agent, or Firm*—Jon S. Saxe; Bernard S. Leon; Frank P. Hoffman

[57] ABSTRACT

The present invention relates to a process for producing aclacinomycins A and B. More particularly, the present invention is concerned with a process for producing selectively aclacinomycins A and B in high yield without formation of cinerubins A and B, by means of a fermentation process, utilizing *Streptomyces galilaeus* OBB-731.

5 Claims, No Drawings

PROCESS TO PRODUCE ACLACINOMYCINS A AND B

DESCRIPTION OF THE INVENTION

The present invention relates to a process for producing aclacinomycins A and B. More particularly, the present invention is concerned with a process for producing selectively aclacinomycins A and B in high yield without formation of cinerubins A and B, by means of a fermentation process, utilizing Streptomyces galilaeus OBB-731.

There has been hitherto well known a process for the preparation of aclacinomycins A and B by means of fermentation, utilizing Streptomyces galilaeus MA144-M1 (FERM-P No. 2455; ATCC 31133) as disclosed in Japanese Patent Publication No. 34915/1976. However, according to this conventional process, the yield of aclacinomycins A and B is low (ca. 55 mg/l in total), whereas according to the present invention, the yield thereof is remarkably high (ca. 530 mg/l in total). Furthermore, the conventional process has further disadvantage such as the fact that cinerubins A and B other than aclacinomycins A and B, are simultaneously formed with considerable yields. The properties of aclacinomycin A and cinerubin A as well as aclacinomycin B and cinerubin B are similar to each other. Therefore, according to the conventional process, troublesome treatments are required for the isolation and subsequent purification of the desirable aclacinomycins A and B from the fermentation broth.

However, it has been surprisingly found that the particular strain, i.e. Streptomyces galilaeus OBB-731 can produce selectively aclacinomycins A and B with very high yield without formation of cinerubins A and B.

The present invention is concerned with a process for producing aclacinomycins A and B by cultivating Streptomyces galilaeus OBB-731 under aerobic condition in an aqueous medium and recovering aclacinomycins A and B from the fermentation broth.

The strain, i.e. Streptomyces galilaeus OBB-731 which also forms a part of the present invention has been isolated from soil in Oberammergau, West Germany and has been deposited in the Agency of Industrial Science and Technology, Fermentation Research Institute, Japan, under "FERM-P No. 5402" and at the American Type Culture Collection, Rockville, Md., U.S.A. under ATCC No. 31615.

The mycological characteristics thereof are as follows:

1. Morphological properties

The strain OBB-731 (FERM-P No. 5402; ATCC 31615) forms moderately long aerial mycelium from substrate mycelium. Hooks or spirals are observed to develop at the apex of the aerial mycelium, but no whorls.

Mature spore chains with more than 10 spores per chain are usually produced. The spores are cylindrical and measured 0.5 to 0.6μ×0.8 to 1.0μ, and its surface is smooth.

2. Cultural characteristics on various media

The cultural characteristics of strain OBB-731 (FERM-P No. 5402; ATCC 31615) is shown in Table 1.

The color of the growth of strain OBB-731 (FERM-P No. 5402; ATCC 31615) on sucrose-nitrate agar, glucose-asparagine agar, glycerol-asparagine agar, starch-inorganic salts agar and oatmeal agar changes to pink-~violet by the dropping of 0.05 N NaOH solution.

TABLE 1

Cultural characteristics of strain OBB-731 (FERM-P No. 5402; ATCC 31615)

| Medium | Strain OBB 731 (FERM-P No. 5402; ATCC 31615) |
|---|---|
| Sucrose nitrate agar | |
| Growth | pale yellow ~ pale yellowish brown [3gc, Light Tan] |
| Aerial Mycelium | brownish gray [3cb, Sand] ~ pale orange [5cb] |
| Diffusible Pigment | yellowish |
| Glucose-asparagine agar | |
| Growth | dull orange [3pe, Topaz ~ 3ne, Topaz] |
| Aerial Mycelium | light brownish gray [3dc, Natural] |
| Diffusible Pigment | brownish |
| Glycerol-asparagine agar (ISP medium No. 5) | |
| Growth | pale yellow [3gc, Light Tan] ~ pale yellowish brown [31c, Amber] |
| Aerial Mycelium | light gray [2fe, Covert Gray] |
| Diffusible Pigment | yellow |
| Starch-Inorganic salts agar (ISP medium No. 4) | |
| Growth | pale yellow [2pc, Bright Gold] ~ dull yellow [2pe, Mustard Gold] |
| Aerial Mycelium | light brownish gray [2dc, Natural] ~ light gray [2fe, Covert Gray] |
| Diffusible Pigment | yellow |
| Tyrosine agar (ISP medium No. 7) | |
| Growth | dark brownish gray [3ni, Clove Brown] |
| Aerial Mycelium | none |
| Diffusible Pigment | black |
| Nutrient agar | |
| Growth | colorless pale brown |
| Aerial Mycelium | none |
| Diffusible Pigment | brown |
| Yeast extract-malt extract agar (ISP medium No. 2) | |
| Growth | yellowish brown [3ng, Yellow Maple] |
| Aerial Mycelium | light gray [2fe, Covert Gray] |
| Diffusible Pigment | none |
| Oatmeal agar (ISP medium No. 3) | |
| Growth | pale yellowish brown [2gc, Bamboo] ~ pale brown [3ie, Camel] |
| Aerial Mycelium | light gray [2fe, Covert Gray ~ 3fe, Silver Gray] |
| Diffusible Pigment | brown |
| Skimmed milk (37° C.) | |
| Growth | brown ~ dark brown |
| Aerial Mycelium | white ~ brownish gray |
| Diffusible Pigment | dark brown |
| Glucose-peptone-gelatin agar | |
| Growth | pale yellow |
| Aerial Mycelium | none |
| Diffusible Pigment | brown |

3. Physiological characteristics

The physiological characteristics and carbohydrate utilization of the strain OBB-731 (FERM-P No. 5402; ATCC 31615) is shown in Table 2 and 3, respectively. The growth temperature was examined on yeast extract-malt extract agar (ISP medium No. 2) at 20°, 27°, 32°, 37°, 40° and 45° C. Optimal temperature for growth is 27° C. to 32° C. and no growth at 45° C.

TABLE 2

Physiological characteristics of strain OBB-731
(FERM-P No. 5402; ATCC 31615)

| Tests | Responses | Methods and materials employed |
|---|---|---|
| Gelatin liquefaction | weak to moderate liquefaction | glucose-peptone-gelatin medium 27° C. |
| Starch hydrolysis | weak to moderate hydrolysis | starch-inorganic salts agar |
| Peptonization and coagulation of skimmed milk | moderate to strong peptonization and no coagulation | 10% skimmed milk 37° C. |
| Nitrate reduction | positive | ISP medium No. 8 27° C. |
| Melanin formation | positive | ISP medium No. 1 ISP medium No. 6 ISP medium No. 7 |

TABLE 3

Carbohydrate utilization of strain OBB-731
(FERM-P No. 5402; ATCC 31615)

| | |
|---|---|
| L-Arabinose | positive |
| D-Xylose | positive |
| Glucose | positive |
| D-Fructose | positive |
| Sucrose | positive |
| Inositol | positive |
| L-Rhamnose | positive |
| Raffinose | positive |
| D-Mannitol | negative |

Basal medium: Pridham-Gottlieb medium (ISP No. 9)
Temperature: 27° C.

Summarizing the above characteristics of the strain, OBB-731 (FERM-P No. 5402; ATCC 31615), it belongs to the genus Streptomyces. The aerial mycelium forms spirals at the apex, but not whorls. The surface of spore is smooth. The growth on various media is found to be pale yellowish brown to pale brown or dull orange, and the aerial mycelium is light gray. The strain produces yellowish to brown diffusible pigment and melanin on various media. Among known species of Streptomyces, strain OBB-731 (FERM-P No. 5402; ATCC 31615) resembles *Streptomyces galilaeus* (Reference 1: Archiv für Mikrobiologie, 31, 356, 1958. Reference 2: The Actinomycetes, 2, 215, 1961. Reference 3: International Journal of Systematic Bacteriology, 22, 298, 1972). The differences between the present strain and the standard strain of *S. galilaeus* ISP 5481 were investigated by parallel cultures. The results are shown in Table 4.

TABLE 4

| | OBB-731 (FERM-P No. 5402; ATCC 31615) | S. galilaeus ISP 5481 |
|---|---|---|
| Liquefaction of gelatin | weak to moderate | weak to moderate |
| Coagulation of milk | negative | weak positive |
| Diffusible pigment | dark brown | light brown |
| Change of color of growth by 0.50N NaOH solution: | | |
| ISP medium No. 3 | pink to violet | no change |
| ISP medium No. 4 | slight pink ~ violet | no change |
| ISP medium No. 5 | violet | slight violet |

From the results, the present strain, OBB-731 (FERM-P No. 5402; ATCC 31615), differs from *S. galilaeus* ISP 5481 in coagulation of skimmed milk, production of diffusible pigment and change of color of growth by 0.05 N NaOH solution. However, the present strain agrees very closely with *S. galilaeus* ISP 5481 in morphology and color of the growth and mycelium on various media, chromogenicity and utilization of carbohydrates. Thus, strain OBB-731 (FERM-P No. 5402; ATCC 31615) can be identified as *Streptomyces galilaeus* and designated *Streptomyces galilaeus* OBB-731.

Production of aclacinomycins by *Streptomyces galilaeus* MA144-M1 (FERM-P No. 2455) is reported (Reference 4: Japanese Patent Publication No. 34915/1976). However the strain MA144-M1 differs from the strain OBB-731 in that MA144-M1 coproduces cinerubins A and B, while the strain OBB-731 only produces aclacinomycins. Moreover, these two strains differ in formation of aerial mycelium, production of diffusible pigment and color of growth, as summarized in Table 5.

TABLE 5

| | S. galilaeus OBB-731 (FERM-P No. 5402; ATCC 31615) | S. galilaeus MA144-M1 (FERM-P NO. 2455; ATCC 31133) |
|---|---|---|
| Formation of aerial mycelium | | |
| ISP medium No. 3 | moderate to good | thin |
| ISP medium No. 7 | none | thin (white) |
| Sucrose nitrate agar | thin (brownish gray) | none |
| Diffusible pigment | | |
| Sucrose nitrate agar | yellowish | none |
| ISP medium No. 5 | yellow | brown |
| Color of growth | | |
| ISP medium No. 5 | pale yellow ~ pale yellowish brown | yellowish orange ~ brown |

According to the process provided by the present invention, aclacinomycins A and B can be selectively produced in high yield without formation of cinerubins A and B by cultivating *Streptomyces galilaeus* OBB-731 (FERM-P No. 5402; ATCC 31615) under aerobic condition in an aqueous medium.

The cultivation may be carried out in a culture medium containing the usual nutrient substances. The carbon sources, for example, are glucose, sucrose, starch, lactose, maltose, fructose, glycerol, dextrin or mixtures thereof, and the nitrogen sources, for example, organic substances such as corn steep liquor, peptone, yeast extract, soybean meal and the like, and inorganic substances such as ammonium sulfate, ammonium chloride and the like. Furthermore, inorganic salts such as sodium chloride, potassium chloride, potassium phosphate, magnesium sulfate, calcium carbonate and the like may be also added to the medium.

The cultivation may be carried out under aerobic condition in an aqueous medium, especially by a submerged fermentation process. The preferred temperature for the cultivation is in the range of 20° C. to 35° C., in particular 25° C. to 30° C. The pH of the medium may vary, however it is generally in the range of 4 to 8. The fermentation is suitably terminated at the time when the maximum yield of the desired aclacinomycins A and B has been attained. The timing thereof can be determined, for example, by high pressure liquid chromatography.

The isolation and purification of aclacinomycins A and B produced in the fermentation broth may be carried out using methods known per se such as the following: From the fermentation broth obtained in the manner mentioned above, the mycelium is removed by centrifugation or filtration. The aclacinomycins A and B may be extracted with a suitable solvent either from the mycelium or from the filtrate. Most of aclacinomycins A and B exist in the mycelial cake. In order to extract the aclacinomycins A and B in the mycelial cake, the active substances are extracted with an alcohol such as methanol, ethanol and the like, and subsequently with a water-immiscible organic solvent such as chloroform and methylene chloride. From the filtrate, the active substances are extracted with a solvent mixture of the water-immiscible organic solvent and an alcohol or water. The water-immiscible organic solvent layer is evaporated to a small volume and diluted with a low polar solvent such as n-hexane, cyclohexane and the like to precipitate a yellow solid, i.e. aclacinomycin A and aclacinomycin B mixture. Alternatively, such aclacinomycins A and B can be directly extracted from the fermentation broth by the aforementioned methods without the separation of mycelium.

According to the process provided by the present invention, cinerubins A and B are not produced, and hence the active substances obtained by the above mentioned methods do not include the cinerubins A and B. Therefore, according to the process of the present invention, it is not necessary to take troublesome treatments for the removal of other pigmented substances such as cinerubins A and B from the active substances, for example by combinations of the processes of chelation with metal ions, solvent precipitation, solvent extraction, and the like.

If necessary aclacinomycin A and aclacinomycin B can be respectively separated from the mixture thereof. For example, the mixture is dissolved in chloroform, placed on a silica gel column and then eluted with a solvent mixture of chloroform and methanol. After that, aclacinomycin B is eluted first with chloroform-methanol (99:1) and then aclacinomycin A is eluted with the above solvent mixture in the ratio of 98:2.

The resulting respective aclacinomycins A and B can be purified further by repeating the above method.

As mentioned above, according to the present invention, pure aclacinomycin A and B can be obtained in high yield without the formation of cinerubins A and B.

The aclacinomycins A and B are useful as antitumor agents.

The present invention will be illustrated in more detail by the following Examples.

EXAMPLE 1

The scraped spores from an agar slant of *Streptomyces galilaeus* OBB-731 (FERM-P No. 5402; ATCC 31615) were transferred to a 500 ml Erlenmeyer flask containing 100 ml of sterilized medium consisting of 20.0 g D-glucose, 20.0 g soluble starch, 5.0 g S-3 meat (Ajinomoto Co., Ltd.), 2.5 g yeast extract (Daigo Eiyo Kagaku Co., Ltd.), 1.0 g $K_2HPO_4$, 1.0 g $MgSO_4·7H_2O$, 3.0 g NaCl and 3.0 g $CaCO_3$ made up to one liter with tap water. The flask was incubated at 27° C. on a rotary shaker set at 180 rpm. After 72 hours, two ml of the culture were transferred to a 500 ml Erlenmeyer flask containing 100 ml of sterile production medium consisting of 20 g D-glucose, 20 g soluble starch, 10 g Pharmamedia (Traders Oil Miss Co., U.S.A.), 1 g $MgSO_4·7H_2O$, 3 g NaCl and 3 g $CaCO_3$ made up to one liter with tap water. The culture was incubated at 27° C. for 72 hours on a rotary shaker set at 180 rpm.

At this time, antibiotic activity of the culture filtrate and the mycelial extract, measured by paper disc agar diffusion method, using Sarcina lutea IAM-1009 as a test microorganism, was 22 mm and 20 mm in diameter, respectively.

EXAMPLE 2

600 ml of the vegetative culture obtained by a manner analogous to that described in Example 1 were transferred to a 50 l jar containing 30 liter of the medium with the same components as described in Example 1 but including 0.1% Nissan Disfoam (Nippon Yushi Co., Ltd.) The cultivation was carried out at 27° C. with the agitation of 350 rpm and aeration of 1 v/v medium. At approximately 90 hours, the incubation was terminated.

(ISOLATION 1)

The culture was centrifuged to separate mycelium from the filtrate. The mycelial cake was suspended in 15 liters of methanol, stirred for 3 hours and filtered. The cake was extracted with methanol once again and filtered. To the extract thus obtained, 30 liters of chloroform and 30 liters of water were added and mixed, and the chloroform layer was obtained. The culture filtrate on the other hand, was extracted with 60 liters of a solvent mixture of chloroform and methanol (1:1), and chloroform layer was obtained. The chloroform extracts from the cell cake and the culture filtrate were combined and evaporated to a small volume. The concentrates were diluted with n-hexane to precipitate a yellow solid and dried in vacuo to give 45 g of aclacinomycin A and aclacinomycin B mixture. There were not obtained other pigmented substances such as cinerubins A and B which are red.

(ISOLATION 2)

45 g of yellow solid obtained in (Isolation 1) were dissolved in 1000 ml of chloroform, and 100 g of silica gel powder were added thereto. The suspension was shaken for 15 hours at room temperature. The suspension was concentrated to dryness in vacuo to apply to a column of 40 cm in length and 5.5 cm in diameter packed with silica gel (Kieselgel 60, reinst; Merck). The column was developed with the solvent mixture of chloroform and methanol. After washing the column with chloroform, aclacinomycin B was eluted with the solvent of chloroform-methanol (99:1). Aclacinomycin A was eluted with the above mixture with the ratio of 98:2. Each of the eluate was concentrated to dryness in vacuo and 25 g of crude aclacinomycin B and 5.4 g of crude aclacinomycin A were obtained as yellow powder.

(ISOLATION 3)

The crude aclacinomycin B (25 g) obtained in (Isolation 2) was further purified. The sample was dissolved in a small amount of chloroform and mixed with silica gel and subjected to a column of 50 cm in length and 3.5 cm in diameter packed with silica gel (Kieselgel 60 reinst, Merck). The column was developed with a solvent mixture of dichloromethane and methanol (98:2). The fractions containing only aclacinomycin B were combined and evaporated to dryness. 9450 mg of pure aclacinomycin B were obtained as yellow powder: m.p. 161° C.

(ISOLATION 4)

The crude aclacinomycin A (5.4 g) obtained in (Isolation 2) was dissolved in a small amount of chloroform and mixed with silica gel and subjected to a column of 50 cm in length and 3.5 cm in diameter packed with silica gel (Kisselgel 60 reinst, Merck). The column was washed with a solvent mixture of dichloromethane-methanol (99:1) and aclacinomycin A was eluted with the above mixture of 97:3. The fractions containing only aclacinomycin A were combined and evaporated to dryness. 1860 mg of pure aclacinomycin A were obtained as yellow powder: m.p. 148° C.

EXAMPLE 3

A 144-hour culture (3 liters) of *Streptomyces galilaeus* OBB-731 (FERM-P No. 5402; ATCC 31615) obtained by a manner analogous to that described in Example 1 was centrifuged to separate mycelium from the filtrate. The mycelial cake was suspended in 1,500 ml of methanol, stirred for 3 hours and filtered. To the extract thus obtained, 1,500 ml of chloroform and 1,500 ml of water were added and mixed, and the chloroform layer was recovered. This extract was concentrated to a small volume and diluted with n-hexane. 3.7 g of yellow solid were obtained.

On the other hand, the culture filtrate was extracted with 3,000 ml of chloroform. The chloroform layer was recovered and evaporated to a small volume and diluted with n-hexane. 800 mg of yellow powder was obtained.

(ISOLATION A) 3.7 g of yellow solid obtained from mycelial fraction were purified by a similar method to that described in—Example 2—(isolation 2, 3, 4).

There were obtained 176.4 mg of pure aclacinomycin A and 831 mg of aclacinomycin B.

(ISOLATION B)

800 mg of yellow solid obtained from culture filtrate fraction were purified by a similar method to that described in Example 2—(isolation 2, 3, 4).

There were obtained 36.3 mg of pure aclacinomycin A and 73.2 mg of aclacinomycin B.

We claim:

1. A process for producing aclacinomycins A and B which comprises cultivating *Streptomyces galilaeus* OBB-731 (FERM-P No. 5402; ATCC 31615) under aerobic condition in an aqueous medium and recovering aclacinomycins A and B from the fermentation broth.

2. The process of claim 1, wherein the fermentation is carried out under aerobic condition.

3. The process of claim 1, wherein the fermentation is carried out at a temperature of 20° C. to 35° C.

4. The process of claim 1, wherein the fermentation is carried out at a pH of 4 to 8.

5. A biologically pure culture of the microorganism *Streptomyces galilaeus* OBB-731 having the identifying characteristics of ATCC 31615, said culture being capable of producing aclacinomycins A and B in a recoverable quantity upon fermentation in an aqueous nutrient medium containing assimilable sources of carbon, nitrogen and inorganic substances.

* * * * *